United States Patent [19]

Marrelli et al.

[11] Patent Number: 5,383,353
[45] Date of Patent: Jan. 24, 1995

[54] MEANS AND METHOD FOR ANALYZING A PETROLEUM STREAM

[75] Inventors: John D. Marrelli, Houston; Dale F. Brost, Sugar Land; Farhan Siddiqui, Katy; Lisa L. Pepin, Sugar Land; Joseph D. Stafford, Bellaire, all of Tex.

[73] Assignee: Texaco Inc., White Plains, N.Y.

[21] Appl. No.: 718,665

[22] Filed: Jun. 21, 1991

[51] Int. Cl.⁶ ............................................. G01N 22/04
[52] U.S. Cl. ................................ 73/61.43; 73/61.71; 324/639; 324/640
[58] Field of Search ............... 73/61.1 R, 61 R, 61.41, 73/61.43, 61.71, 861.04, 61.44; 324/640, 639

[56] References Cited
U.S. PATENT DOCUMENTS 4,301,400 11/1981 Paap ........................ 324/640
4,499,418 2/1985 Helms .................. 73/61.1 R X
4,862,060 8/1989 Scott ..................... 73/61 R X
4,947,127 8/1990 Helms .................. 73/61.1 R X
4,947,128 8/1990 Hatton ....................... 324/640
4,947,129 8/1990 Helms ....................... 324/640
5,001,434 3/1991 Marelli ...................... 324/640
5,014,010 5/1991 Helms ....................... 324/640

Primary Examiner—Hezrone E. Williams
Assistant Examiner—Michael J. Brock
Attorney, Agent, or Firm—Kenneth R. Priem; Ronald G. Gillespie; Russell J. Egan

[57] ABSTRACT

The means and method of the present invention includes a source of microwave energy and associated elements which provide microwave energy to a petroleum stream. Other circuitry include elements which receive microwave energy from the petroleum stream. Electronic apparatus provides at least two outputs utilizing the provided microwave energy, the received microwave energy and known values for 100 percent oil, 100 percent solids of one specie and 100 percent water, corresponding to different ratios of ratios involving oil and water, oil and solids, and water and solids.

6 Claims, 1 Drawing Sheet

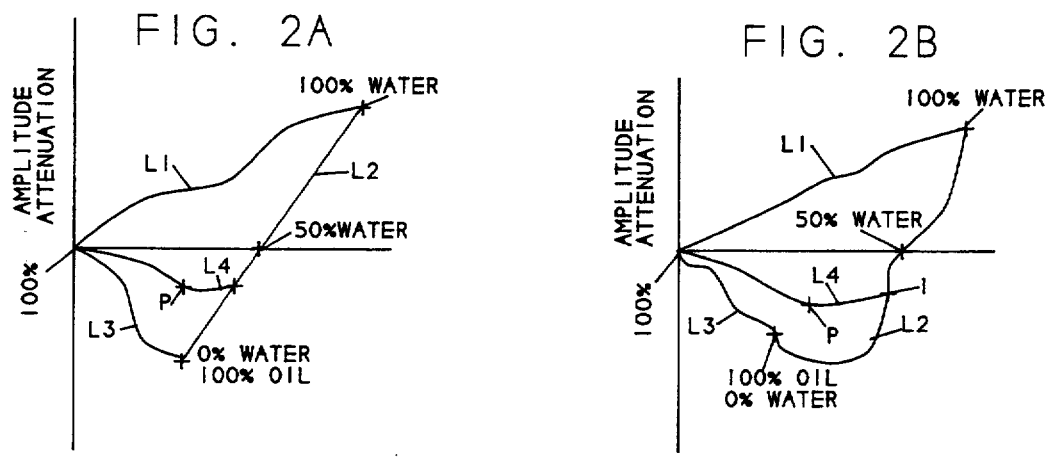
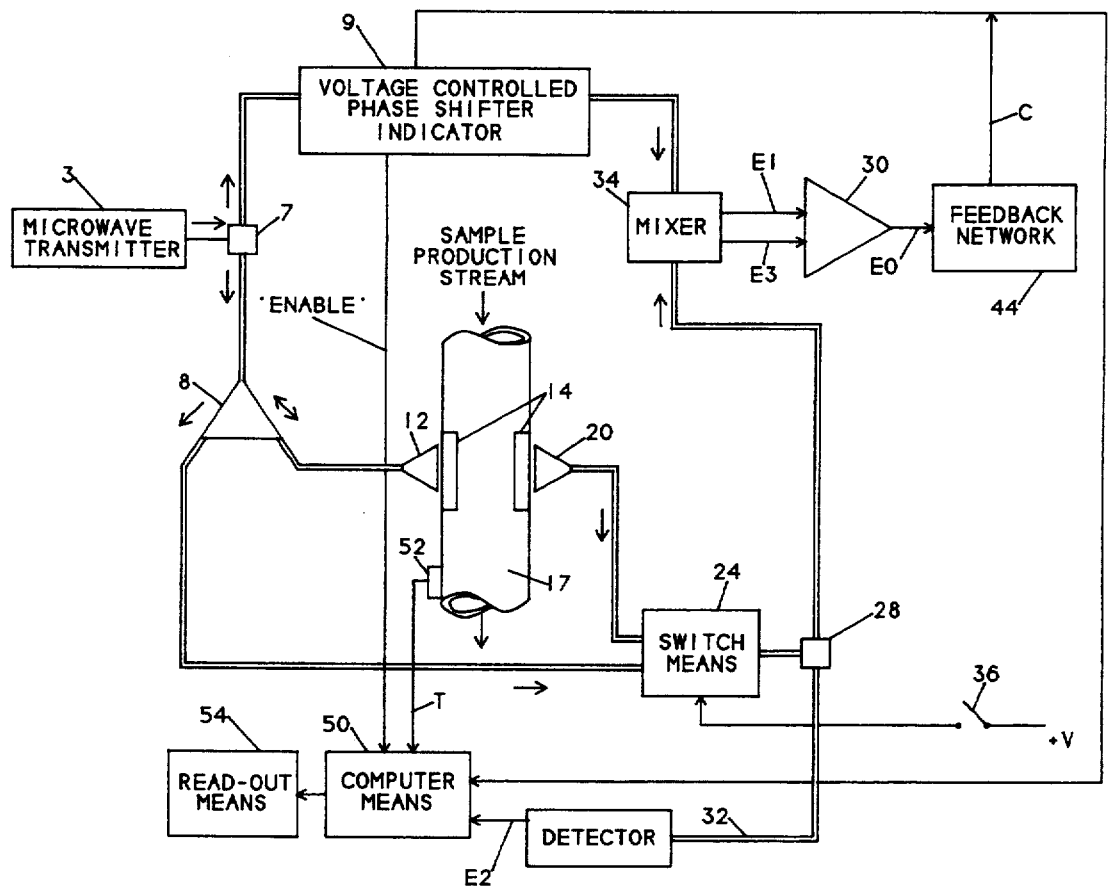

MEANS AND METHOD FOR ANALYZING A PETROLEUM STREAM

BACKGROUND OF THE INVENTION

Field of the Invention

The present invention relates to analyzers and analyzing methods in general and, more particularly, to petroleum stream analyzers and analyzing methods.

SUMMARY OF THE INVENTION

The means and method of the present invention includes a source of microwave energy and associated elements which provide microwave energy to a petroleum stream. Other circuitry include elements which receive microwave energy from the petroleum stream. Electronic apparatus provides at least two outputs utilizing the provided microwave energy, the received microwave energy and known values for 100 percent oil, 100 percent solids of one species and 100 percent water, corresponding to different ratios of ratios involving oil and water, oil and solids, and water and solids.

The objects and advantages of the present invention will appear more fully hereinafter from a consideration of the detailed description which follows, taken together with the accompanying drawings wherein one embodiment of the invention is illustrated by way of example. It is to be expressly understood, however, that the drawings are for illustration purposes only and not to be construed as defining the limits of the invention.

DESCRIPTION OF THE DRAWINGS

FIG. 1 is a simplified block diagram of a petroleum stream analyzer constructed in accordance with the present invention.

FIG. 2A is a graphical representation of a map utilized in practicing the present invention for a petroleum stream which is in a water-continuous phase.

FIG. 2B is a graphical representation of a map for a petroleum stream which is in an oil-continuous phase.

DESCRIPTION OF THE INVENTION

Extraction of oil from tar sands and/or diatomaceous earth, hereinafter referred to as D.E., can be accomplished by keeping the components stationary for example by pelletization of the D.E. and passing a solvent through the mixture or by flowing some combination of the mixture, water and solvent through a pipe from which desired or undesired components are extracted. However, these type of producing methods results in solids of tar sand or D.E. occurring in the produced petroleum stream. The present invention will yield the relationships water to oil, water to solids and/or solids to oil, as herein.

The analyzer shown in FIG. 1 includes a microwave source 3 providing electromagnetic energy, hereinafter referred to as microwave energy. Source 3 is low powered and may use a microwave gun source. Source 3 provides the microwave energy to a directional coupler 7. Directional coupler 7 provides the selected microwave energy to a circulator 8 and to a conventional type voltage controlled phase shifter 9. All conductance or carrying of microwave energy is accomplished by using conventional type waveguides.

Circulator 8 provides microwave energy to an antenna 12. Antenna 12 provides the microwave energy through a window 14, which may be of a low loss dielectric material such as ceramic or Teflon, to a petroleum stream passing through a pipe 17. Pipe 17 may be a portion of a pipeline having windows 14 or it may be made of the "window" material. The microwave energy provided by antenna 12 passes through the petroleum stream and another window 14 and is received by an antenna 20. Antenna 20 provides the received microwave energy to a switch means 24 which in turn provides the received microwave as test microwave energy to a directional coupler 28, as hereinafter explained. Directional coupler 28 provides the test microwave energy to a detector 32 and to a mixer 34. Detector 32 provides a signal E2 corresponding to the intensity of the microwave energy received by antenna 20.

The petroleum stream also reflects some of the microwave energy back to antenna 12 which passes back through antenna 12 to circulator 8. Circulator 8 blocks the reflected microwave energy from feeding back to source 3 and provides the reflected microwave energy to switch means 24. Reflected microwave energy becomes more important as the distance between antennas 12 and 20 increases. This is especially true where a large pipeline carrying the petroleum stream is being monitored.

A positive direct current voltage $+V$ is provided to a switch 36 which is connected to switch means 24. With switch 36 open, switch means 24 provides microwave energy from antenna 20 as test microwave energy. When switch 36 is closed, the reflected microwave energy from circulator 8 is provided by switch means 24 as the test microwave energy.

The microwave energy from voltage controlled phase shifter 9, hereinafter called the reference microwave energy, and the test microwave energy from directional couple 28, are provided to mixer 34 which mixes them to provide two electrical signals E3, E1, representative of the phases of the reference microwave energy and the test microwave energy, respectively.

A differential amplifier 30 provides an output signal E0 in accordance with the difference between signals E3 and E1. Signal E0 is a function of the phase difference between the reference microwave energy and the test microwave energy and is provided to a feedback network 44. Feedback network 44 provides a signal C to voltage control phase shifter 9, controlling the phase of the reference microwave energy, and to a mini-computer means 50. Signal E0, and hence the signal C, decreases in amplitude until there is substantially 90° phase difference between the reference microwave energy and the test microwave energy. Voltage control phase shifter 9 indicates the amount of phase shift required to eliminate the phase difference.

Signal E2 from detector 32 is also provided to computer means 50.

A temperature sensor 52 senses the temperature of the petroleum stream in pipe 17 and provides a signal T to computer means 50 representative of the sensed temperature.

Phase Shifter 9 also provides an enable signal to computer means 50 allowing computer means 50 to utilize signals T, C and E2.

FIG. 2A is a "map" of a water-continuous phase petroleum stream with 100% solid D.E., 100% water and 100% oil points shown as D.E., water and oil, respectively. FIG. 2B is a "map" of an oil-continuous phase petroleum stream having solid D.E. The maps of FIGS. 2A and 2B were developed from empirical data utilizing the following equations:

1. $y_{L1} = f(X)$, where $f(X)$ denotes y is a function of X. Where X is equal to phase shift and y is a attenuation which describes a line L1, which can be curved, connecting 100% D.E. to 100% water.
2. $y_{L2} = g(X)$, where $g(X)$ denotes y as another function of X and L2 is a line connecting 100% oil to 100% water.
3. $y_{L3} = h(X)$, where denotes y as yet another function of X and L3 is a line connecting 100% D.E. to 100% oil.

In general, the maps depicted in FIGS. 2A and 2B are utilized by computer means 50 as follows. The amplitude attenuation and phase shift measurements of the microwave energies in pipe 17 are shown in FIGS. 2A and 2B as point P. The procedure is the same, whether the petroleum stream is water-continuous or it is oil-continuous. A line L4 of functional form identical to line L3 is projected by computer means 50 through the 100% D.E. point through point P to intercept line L2, which is in essence a water-oil line connecting the 100% water point and the 100% oil point, at point I. Point I yields the water cut of the petroleum stream. Further, the D.E. to liquid ratio may also be determined as the ratio of the distance from point P to point I along line L4 divided by the distance from the 100% D.E. point to point I along line L4. If there is no solids present in the petroleum stream, point P would lie on line L3 and the surfactant to liquid ratio would be zero.

Although the foregoing has been discussed as being a water cut and a D.E. to liquid fraction measurement, the maps may also yield other ratios. Computer means 50 may generate lines from the 100% water point to intercept line L3. Again, that ratio would be determined in the same manner as previously discussed for the D.E. to liquid ratio. Computer means 50 may also generate a straight line from the 100% oil point through point P and intercept line L1.

What is claimed is:

1. Means of analyzing a petroleum stream having oil, water, and solids of one species comprising:

providing means for providing microwave energy to the petroleum stream, receiving means for receiving microwave energy from the petroleum stream, and output means connected to the providing means and to the receiving means for providing at least one output, utilizing the provided microwave energy, the received microwave energy and known values for 100 percent oil, 100 percent solids, and 100 percent water, corresponding to a ratio of solids to liquid.

2. The analyzing means as described in claim 1 in which the output means includes computer means.

3. A method for analyzing a petroleum stream having oil, water and solids comprising the steps of:

providing microwave energy to the petroleum stream, receiving microwave energy from the petroleum stream, providing at least one output, utilizing the provided microwave energy, the received microwave energy and known values for 100 percent oil, 100 percent solids and 100 percent water, corresponding to a ratio of solids to liquid.

4. A method as described in claim 3 in which the step of providing at least one output includes:

relating known values of 100 percent oil, 100 percent solids and 100 percent water to the phase difference between the provided microwave energy and the received microwave energy and to the intensity of the received microwave energy.

5. A method as described in claim 4 in which the step of providing at least one output further includes:

generating a map utilizing points derived from the known values of 100 percent oil, 100 percent water and 100 percent solids, determining a measurement point within the map utilizing the provided microwave energy and the received microwave energy, and providing two outputs in accordance with the relationship of the measurement point to the map.

6. A method as described in claim 5 in which the generating step includes:

deriving a line L1 connecting the reference points for 100 percent solids and 100 percent water, deriving a line L2 for connecting the reference points for 100 percent oil and 100 percent water, and deriving a line L3 connecting the reference points for 100 percent oil and 100 percent solids.

* * * * *